(12) United States Patent
Ono (10) Patent No.: US 8,518,878 B2
(45) Date of Patent: Aug. 27, 2013

(54) METHOD FOR TREATING SKIN AGING BY ADMINISTRATION OF BFGF

(75) Inventor: Ichiro Ono, Hokkaido (JP)

(73) Assignee: Labo Juversa Co., Ltd., Hokkaido (JP)

( * ) Notice: Subject to any disclaimer, the term of this patent is extended or adjusted under 35 U.S.C. 154(b) by 0 days.

(21) Appl. No.: 13/233,315

(22) Filed: Sep. 15, 2011

(65) Prior Publication Data

US 2012/0004173 A1 Jan. 5, 2012

Related U.S. Application Data (63) Continuation of application No. 12/934,299, filed as application No. PCT/JP2009/001303 on Mar. 24, 2009, now abandoned.

(30) Foreign Application Priority Data

Mar. 28, 2008 (JP) ................................ 2008-085952

(51) Int. Cl.
*A61K 38/18* (2006.01)
*C07K 14/50* (2006.01)

(52) U.S. Cl.
USPC ............................ 514/9.1; 514/18.6; 530/399

(58) Field of Classification Search
None
See application file for complete search history.

(56) References Cited

U.S. PATENT DOCUMENTS

| | | | |
|---|---|---|---|
| 5,155,214 A | 10/1992 | Baird et al. | |
| 6,294,359 B1 * | 9/2001 | Fiddes et al. | 435/69.4 |
| 2007/0224150 A1 * | 9/2007 | Chung | 424/70.14 |

FOREIGN PATENT DOCUMENTS

| | | |
|---|---|---|
| JP | 05-043442 | 2/1993 |
| JP | 07-304686 | 11/1995 |
| JP | 2002-249498 | 9/2002 |
| JP | 2003-342194 | 12/2003 |
| JP | 2004-043313 | 2/2004 |

OTHER PUBLICATIONS

Akimoto et al., "Expression of Basic Fibroblast Growth Factor and Its Receptor by Fibroblast, Macrophages and Mast Cells in Hypertrophic Scar," European Journal of Dermatology, 9(5), pp. 357-362, 1999.
Desmouliere et al., "Apoptosis Mediates the Decrease in Cellularity during the Transition Between Granulation Tissue and Scar," American Journal of Pathology, 146(1), pp. 56-66, 1995.
Ono et al., "Basic Fibroblast Growth Factor Reduces Scar Formation in Acute Incisional Wounds," Wound Repair Regen., vol. 15, No. 5, pp. 617-623, 2007.
Ono et al., "The Scar Reduction Effects of Basic Fibroblast Growth Factor (bFGF) on Acute Incisional Wounds," Japanese Journal of Dermatology, vol. 113, No. 5, p. 757, 2003.
Ono et al., "Treatment of Scar, Keloid by a Local Administration of Growth.Factor," Japan Society of Plastic and Reconstructive Surgery, vol. 17, p. 90, Oct. 2, 2008.
Tiede et al., "Basic Fibroblast Growth Factor: a Potential New Therapeutic Tool for the Treatment of Hypertrophic and Keloid Scars," Ann. Anat., vol. 191, No. 1, pp. 33-44, 2009.

* cited by examiner

*Primary Examiner* — Christine J Saoud
(74) *Attorney, Agent, or Firm* — Kenneth H. Sonnenfeld; Margaret B. Brivanlou; King & Spalding LLP (57) ABSTRACT

It is to provide a method for treating skin aging, or a method for treating skin scar that can exert a sufficient effect. A composition for treating skin aging comprising bFGF for treating aging of the skin that is administered intradermally or subcutaneously, or a composition for treating skin scar comprising bFGF for treating scar of skin that is administered intradermally or subcutaneously is utilized. Preferred examples of aging of skin include skin wrinkle, pigmented spot, sagging skin, rough skin, skin thinning, decrease of skin viscoelasticity, etc., and preferred examples of scar include keloid, hypertrophic scar, scar contracture, etc.

11 Claims, 10 Drawing Sheets

METHOD FOR TREATING SKIN AGING BY ADMINISTRATION OF BFGF

PRIORITY CLAIM

This application is a Continuation of co-pending U.S. patent application Ser. No. 12/934,299 filed Sep. 24, 2010, which is a National Stage Entry of PCT/JP2009/001303 filed Mar. 24, 2009. This application also claims priority to JP2008-085952 filed Mar. 28, 2008. The entire contents of these applications are hereby incorporated by reference.

TECHNICAL FIELD

The present invention relates to an agent for preventing and treating aging of skin, and an agent for treating scars of skin.

BACKGROUND ART

Aging of skin such as skin wrinkle, sagging and loose skin, pigmentation, depigmentation, skin thinning, decrease of skin viscoelasticity, etc. influences seriously the quality of life (QOL) particularly in women, and when the degree is severe, it sometimes becomes an obstacle in social life. Conventionally, most of aging of skin was thought to be a so-called physiological aging which progresses with increasing age. However, recently, it is thought that almost all aging of skin is caused by aging due to exposure to ultraviolet rays (so-called photoaging). When skin is exposed to ultraviolet rays, mechanisms including inflammation, followed by disruption of dermal tissues and functional decrease of fibroblast cells are induced, and aging of skin such as described in the above progress.

On the other hand, similarly to aging of skin, scars of skin such as hypertrophic scars and keloid etc., also greatly influence the QOL of the patient, and it sometimes becomes an obstacle in social life depending on the degree or site (face, etc.) of the scar. Scars are generated during the healing process of following injury, etc. Specifically, when skin is damaged by injuries generated by surgery, etc., wound healing mechanisms such as hemorrhagic phase and coagulation phase, inflammatory phase, proliferating phase, etc. function, and epidermalization ends after a certain period. Then, the wound is healed with scar remaining after a maturation phase during which scar matures. At that time, depending on conditions such as delayed healing, patient's age and body sites, etc. the wound may form scars such as hypertrophic scar, scar contracture, keloid, atrophic scar, etc. In many cases, changes in thickness calm down with the passage of time, while symptoms such as reddening, pruritus, colic pain, etc. are severe in some cases, and the QOL of the patient can be significantly lowered for a long period of time. Further, wide scar or atrophic scar often remains even when the changes are calmed down, and the QOL of the patient was lowered for a long period of time in any of the cases.

As stated in the above, it can be said that aging of skin and scar of skin are not only cosmetic and functional problems of the patient but social problems such as QOL of the patient, etc. Therefore, many attempts for preventing and treating aging of skin and scars of skin have been made. Concerning prevention and treatment of aging of skin, for example, Patent Document 1 discloses that wrinkles and sagging skin are treated by applying externally a skin care product comprising basic fibroblast growth factor (bFGF) as active ingredient to the skin. bFGF is one kind of growth factor that has been found and identified by Grotendorst et al., which is a single chain polypeptide without sugar, having a molecular weight of about 17 K Dalton, and having a phospholipid affinity. Further, Patent Document 2 describes that an external preparation for skin comprising a fibroblast growth factor and epidermis growth factor exhibits an effect on improving wrinkles, pigmented spots, hair loss, etc. However, neither of the above-mentioned skin care product nor skin external preparation could prevent and treat aging of skin sufficiently.

On the other hand, the treatment of scar of skin has been conventionally based on surgical therapy. Therapeutic methods such as external use and topical administration of adrenal corticosteroid, application of adrenal corticosteroid-containing patch, parenteral use of anti-allergic agent, radiotherapy, etc. have been applied in some cases. However, these therapeutic methods require quite a long time period, and even by utilizing all of the therapeutic methods, it was difficult to treat sufficiently the scars. On the other hand, concerning the prevention of scars of skin, for example, Patent Document 3 discloses that when administering subcutaneously a basic fibroblast growth factor (bFGF) additionally to a hepatocyte growth factor (HGF) to the skin just after the wound is formed, tissue regeneration in the wound site is promoted, or formation of scars after the healing of wound is suppressed. The Patent Document 3 describes that in the mechanism of action, it is estimated that, first, the wounded healing action of bFGF functions during the early phase of injury, and then, during the scar maturation phase, HGF acts to suppress excessive growth and fibrosis of granulation tissue. However, effect of bFGF without being combined with HGF when a scar has already been formed has not been reported yet.

Further, Patent Document 4 discloses a pharmaceutical composition or veterinary composition for preventing and healing or treating organic diseases causing pathological and histological changes in vivo tissues, comprising ginsenoisides or their metabolic products, or salt thereof. In the section of "Prior Art" in Patent Document 4, it is described as follows: "Conventionally, it was known that topical application or topical spraying of basic fibroblast growth factor (bFGF) and platelet derived growth factor (PDGF) promotes partially the regeneration and reassembly of skin tissues, and exerts an effect and efficacy to skin ulcer and pressure sore. However, it cannot be said that the effect is satisfactory, even from a clinical standpoint (Singer, A. J. and Clark, R. A. F. New Eng. J. Med., 341, 738-746, 1999). Further, the aforementioned peptide factors (bFGF, PDGF) are pharmaceutical compositions that can be used only for topical application and topical spraying, and almost no effect or efficacy can be expected from a systemic administration such as intravenous administration."

Under such circumstances, an agent for preventing and treating skin aging, or an agent for treating skin scars that can exert sufficient effect was awaited.

Patent Document 1: Japanese Laid-Open Patent Application No. 5-434442
Patent Document 2: Japanese Laid-Open Patent Application No. 2004-043313
Patent Document 3: Japanese Laid-Open Patent Application No. 2003-342194
Patent Document 4: Japanese Laid-Open Patent Application No. 2002-249498

DISCLOSURE OF THE INVENTION

Object to be Solved by the Invention

The object of the present invention is to provide an agent for preventing and treating skin aging, and an agent for treating skin scars that can exert sufficient effect.

Means to Solve the Object

As it is stated in the section of "Background Art", bFGF is a pharmaceutical composition with which only topical application or topical spraying is possible, and it was considered that almost no effect or efficacy can be expected from a systemic administration such as intravenous administration. Specifically, it was thought that even by administering intradermally or subcutaneously bFGF per se, any diseases or symptoms could be prevented or treated significantly. Under such common knowledge of persons skilled in the art, the present inventors found out coincidentally that when intentionally administering intradermally or subcutaneously bFGF, and not using it for external application on the skin surface, it exerts a significant preventative and therapeutic effect on skin aging and a significant therapeutic effect on skin scars. They have thus completed the present invention based on this finding. Herein, "intradermal administration" means to administer an agent (preferably by injection) into dermal tissue of the skin. Further, "subcutaneous administration" herein means to administer an agent (preferably by injection) into adipose tissue under the skin.

Specifically, the present invention relates to:
(1) an agent for preventing and treating skin aging containing bFGF for treating aging of skin, which is administered intradermally or subcutaneously;
(2) the agent for preventing and treating skin aging according to (1), wherein the aging of skin is a photoaging of skin;
(3) the agent for preventing and treating skin aging according to (1) or (2), wherein the aging of skin is one or more selected from skin wrinkle, pigmented spot, sagging skin, rough skin, skin thinning and decrease of skin viscoelasticity; and
(4) the agent for preventing and treating skin aging according to any one of (1) to (3), wherein the dosage amount of bFGF is 0.1 µg to 1 mg per 1 $cm^2$ of skin that is a target of prevention or treatment.

Further, the present invention relates to:
(5) an agent for treating skin scar containing bFGF for treating scar of skin, which is administered intradermally or subcutaneously;
(6) the agent for treating skin scar according to (5), wherein the scar is one or more selected from keloid, hypertrophic scar and scar contracture; and
(7) the agent for treating skin scar according to (5) or (6), wherein the dosage amount of bFGF is 0.1 µg to 1 mg per 1 $cm^2$ of skin that is a target of treatment.

Furthermore, the present invention relates to:
(8) use of bFGF in the manufacture of an agent for preventing and treating aging of skin; and
(9) use of bFGF in the manufacture of an agent for treating scar of skin.

BRIEF EXPLANATION OF DRAWINGS

In FIG. 2, the upper left picture shows the condition before the treatment, the upper right picture shows the condition 1 month after the treatment, the lower left picture shows the condition 2 months after the treatment, and the lower right picture shows the condition 3 months after the treatment.

In FIG. 3, the upper left picture shows the condition before the treatment, and the lower right picture shows the condition 2 months after the treatment.

In FIG. 4, the left picture shows the condition before the treatment, and the right picture shows the condition 2 months after the treatment.

In FIG. 5, the left picture shows the condition before the treatment, and the right picture shows the condition 3 months after the treatment.

In FIG. 6, the left picture shows the condition before the treatment, and the right picture shows the condition 3 months after the treatment.

In FIG. 7, the left picture shows the condition before the treatment, and the right picture shows the condition 3 months after the treatment.

In FIG. 8, the left picture shows the condition before the treatment, and the right picture shows the condition 3 months after the treatment.

BEST MODE OF CARRYING OUT THE INVENTION

The agent for preventing and treating skin aging of the present invention is not particularly limited, as long as it comprises bFGF for treating aging of skin, and is administered intradermally or subcutaneously. Further, the agent for treating skin scar of the present invention is not particularly limited, as long as it comprises bFGF for treating aging of skin, and is administered intradermally or subcutaneously.

bFGF used in the present invention is a substance that is widely and generally known, and that can also be obtained as a commercial product (e.g. bFGF commercial product "Trafermin" (genetically modified): KAKEN PHARMACEUTICAL CO., LTD., etc.) As long as it has an effect on preventing and treating skin aging or an effect on treating skin scar of the present invention, the aspect of bFGF may be any of a naturally occurring type- or genetically modified type-bFGF, or a precursor protein thereof; a protein wherein one or more constituent amino acids of the naturally occurring type- or genetically modified type-bFGF has been substituted, deleted or inserted; a protein encoded by a cDNA that can hybridize under stringent conditions (65° C., 1×SSC, 0.1% SDS or 0.1×SSC, 0.1% SDS) to a naturally occurring type-human bFGF; a protein having a homology of 75% or more, preferably 80% or more, more preferably 85% or more, further preferably 90% or more, and further more preferably 95% or more to the naturally occurring type-human bFGF cDNA. Further, it may be a nucleic acid encoding a gene of each protein (cDNA or cDNA plasmid; herein, hereinafter referred to as "gene" as a whole). The genes can be administered as a single plasmid, or in a form of a complex plasmid in which liposome, etc. are combined with an expression vector. In the present invention, the expression vector used for enhancing the introduction efficiency of the gene can be exemplified by any expression vector including viral vector. However, it is preferably an expression vector for mammalian cells. Further, the promoter contained in the expression vector used in the present invention is operably linked to bFGF gene, and is a functional promoter in mammalian (preferably human) cells. This promoter is inductive or constitutive, and may be tissue specific according to need. Further, it is known that the rate of gene expression is different depending on the type of promoters, and for example, the expression rate of a gene under control of an immediate early promoter, an early promoter, and a late promoter is different from each other. Therefore, when administering bFGF as a gene to a mammal, the expression rate and sustainability of the bFGF protein can be adjusted by selecting appropriately the type of these promoters.

bFGF used in the present invention may be formulated into an appropriate formulation according to a common method. The formulation may be a solid formulation such as powder, granule, etc. However, from the viewpoint of obtaining a superior efficiency for preventing and treating skin aging, or a superior efficiency for treating skin scar, it is preferred to formulate it into a liquid agent for injection such as a solution agent, emulsion, suspension agent, etc.; or a gelling agent for injection. As a method for producing the aforementioned liquid agent, for example, a method comprising mixing bFGF with a solvent, and a method comprising further mixing bFGF with a suspending agent, or emulsifying agent can be preferably exemplified. As a method for producing the aforementioned gelling agent, for example, a method of mixing bFGF with gelatin can be preferably exemplified. As stated in the above, when formulating bFGF of the present invention into a formulation, an appropriate pharmaceutically acceptable carrier, e.g. any component such as excipient, binding agent, solvent, solubilizing agent, suspending agent, emulsifying agent, tonicity agent, buffering agent, stabilizing agent, soothing agent, antiseptic agent, antioxidant agent, coloring agent, etc. may be compounded according to needs in formulation.

Examples of the above solvents include: hydrophilic solvent such as purified water, physiological saline, Ringer's solution, ethanol, propylene glycol, glycerin, polyethylene glycol, macrogol, etc.; lipophilic solvent such as olive oil, peanut oil, sesame oil, camellia oil, canola oil, fatty acid monoglyceride, fatty acid diglyceride, higher fatty acid ester, liquid paraffin, etc. Examples of the above suspending agent include: stearyl triethanol amine, sodium lauryl sulfate, lauryl aminopropionate, lecitin, benzalkonium chloride, benzethonium chloride, glyceryl monostearate, polyvinyl alcohol, polyvinylpyrrolidone, sodium carboxymethyl cellulose, methyl cellulose, hydroxymethyl cellulose, hydroxyethyl cellulose, hydroxypropyl cellulose, polysolvates, polyoxyethylene hydrogenated castor oil, gum arabic, bentonite, etc. Further, examples of the above emulsifying agent include gum arabic, gelatin, lecithin, cholesterol, yolk, bentonite, Veegum, cetanol, glyceryl monostearate, methyl cellulose, sodium carboxymethyl cellulose, stearic acid, etc.

Examples of the above solubilizing agent include: polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate, etc. Examples of the above excipient include: lactose, white soft sugar, D-sorbitol, starch, pregelatinized starch, corn starch, D-mannnitol, dextrin, crystalline cellulose, gum arabic, low-substituted hydroxypropyl cellulose, sodium carboxymethyl cellulose, methyl cellulose, serum albumin, etc. Examples of the above binding agent include: pregelatinized starch, sucrose, gelatin, gum arabic, methyl cellulose, carboxymethyl cellulose, sodium carboxymethyl cellulose, crystalline cellulose, white soft sugar, D-mannitol, trehalose, dextrin, pullulan, hydroxypropyl cellulose, hydroxypropyl methyl cellulose, polyvinyl pyrrolidone, polyvinyl alcohol, etc.

Examples of the above tonicity agent include: sodium chloride, potassium chloride, glucose, fructose, mannitol, sorbitol, lactose, saccharose, glycerin, urea, etc. Further, examples of the above buffering agent include: sodium citrate, glycerin, etc. Examples of the above antiseptic agent include: paraoxy benzoic acid esters, chlorobutanol, benzyl alcohol, phenethyl alcohol, dehydroacetic acid, sorbic acid, etc. Examples of the above stabilizing agent include: polyethylene glycol, dextran sulfate sodium, amino acid, human serum albumin, etc. Examples of the above soothing agent include: glucose sugar, calcium gluconate, procaine hydrochloride, etc. Furthermore, examples of the above antioxidant agent include: sulfite, ascorbic acid, etc. Examples of the above coloring agent include: tar pigment, caramel, colcothar, titanium dioxide, FD & C pigments such as FD & C blue No. 2, and FD & C red No. 40 from Ellis & Everard, etc.

Further, bFGF used in the present invention may be formulated into a tissue extender, or sustained-release formulation, by using polysaccharides such as alginic acid, hyaluronic acid, chitin, carboxymethyl starch, carboxymethyl cellulose, etc., proteins such as gelatin, collagen, albumin, fibrin, etc., synthetic high molecules such as polyalanine, polyglycolic acid, polypropylene carbonate, etc., and carriers such as tricalcium phosphate, hydroxyapatite, etc.

Further, the agent for preventing and treating skin aging, or the agent for treating skin scar of the present invention can contain, besides bFGF, a substance having or expected to have an effect on preventing and treating skin aging or an effect to treat skin scar. Examples of substances having or expected to have the above effect preferably include one or more selected from the group consisting of morphogens such as DPP (decapentaplegic), transforming growth factor beta, Hh (Hedgehog), shh (sonic Hedgehog), Wnt (Wingless int), bone morphogenetic protein (BMP), epidermal growth factor, and insulin-like growth factor (ILGF), etc; platelet derived growth factor (PDGF), vascular endothelial growth factor (VGEF), hepatocyte growth factor (HGF), etc. By administering those substances intradermally or subcutaneously in addition to the agent for preventing and treating skin aging, or the agent for treating skin scar of the present invention, they may be used in combination with the agent for preventing and treating skin aging, or the agent for treating skin scar of the present invention.

The method for administering the agent for preventing and treating skin aging of the present invention, or the agent for treating skin scar of the present invention intradermally or subcutaneously is not particularly limited as long as it is a method for administering the agent intradermally or subcutaneously to the site of skin aging or scar, or surrounding part theirof, being the target of prevention or treatment. The dosage amount is not particularly limited, and generally, it can be administered in an amount of 0.1 µg to 1 mg, preferably 1 µg to 100 µg, more preferably 1 µg to 10 µg in terms of bFGF (freeze-dried) per 1 cm² of skin that is the target of prevention or treatment. Further, the frequency of administration is not particularly limited, and it can exert a sufficient effect by a single administration. However, from the viewpoint of sustaining a superior effect, it is preferred to administer the agent continuously and periodically, for example, once every month. The bFGF concentration in the agent for preventing and treating skin aging of the present invention or the agent for treating skin scar of the present invention is not particularly limited, and it is preferred to appropriately adjust the volume of the agent to be administered intradermally or subcutaneously to 0.1 to 0.3 ml, preferably 0.15 to 0.25 ml per 1 cm² of skin. Further, when administering the agent for preventing and treating skin aging of the present invention or the agent for treating skin scar of the present invention intradermally or subcutaneously, it is preferred to use a pressure injector, from the viewpoint of injecting the agent in a simple and accurate manner.

Aging of skin that is the target of the agent for preventing and treating skin aging of the present invention is not particularly limited as long as it is an aging of skin, and it may be a physiological change caused by increasing age, or a photo-aging caused by irradiation of ultraviolet ray. Specifically preferred examples include one or more selected from skin wrinkle, pigmented spot, sagging skin, rough skin, skin thinning and decrease of skin viscoelasticity. Further, scar of skin that is the target of the agent for treating skin scar of the present invention is not particularly limited as long as it is a scar of skin, and specifically preferred examples include one or more selected from keloid, hypertrophic scar, and scar contracture. Herein, substances having a preventive effect to skin aging (skin aging preventive effect) relate to those having an effect on decreasing any aging of skin in advance. Further, substances having a therapeutic effect on skin aging (skin aging therapeutic effect) in the present invention refer to those having an effect on ameliorating any aging of the skin, and substances having a therapeutic effect on skin scar (skin scar therapeutic effect) in the present invention refer to those having an effect of ameliorating any of the skin scars.

Further, the present invention also encompasses use of bFGF in the manufacture of an agent for preventing and treating aging of skin; use of bFGF in the manufacture of an agent for treating scar of skin; a method for using bFGF in an agent for preventing and treating aging of skin; a method for using bFGF in an agent for treating scar of skin; use of bFGF in the prevention and treatment of aging of skin; use of bFGF in the treatment of scar of skin; a method for preventing and treating skin aging comprising administering intradermally or subcutaneously bFGF to mammals (particularly human); and a method for treating skin scar comprising administering intradermally or subcutaneously bFGF to mammals (particularly human). The meaning of the terms or preferred embodiments in these uses or methods is as described in the above.

In the following, the present invention will be explained in detail by referring to the Examples, while the technical scope of the present invention is not limited to these exemplifications.

Example 1

Production of the Formulation of the Present Invention

500 µg of the freeze-dried commercial product of bFGF (Trafermin: KAKEN PHARMACEUTICAL CO., LTD.) was dissolved into 50 ml of distilled water for injection, to prepare 10 µg/ml of bFGF solution. The bFGF solution was dispensed into sterilized polypropylene containers by 1 ml each, and was immediately cryopreserved in a freezer of −70° C. In the following tests, a bFGF solution prepared by naturally melting the cryopreserved product at room temperature was used as the formulation of the present invention (agent for preventing and treating skin aging, or agent for treating skin scar).

Example 2

Test for Confirming the Effect of Preventing and Treating Aging of Skin

1. Case 1

Figure 1:
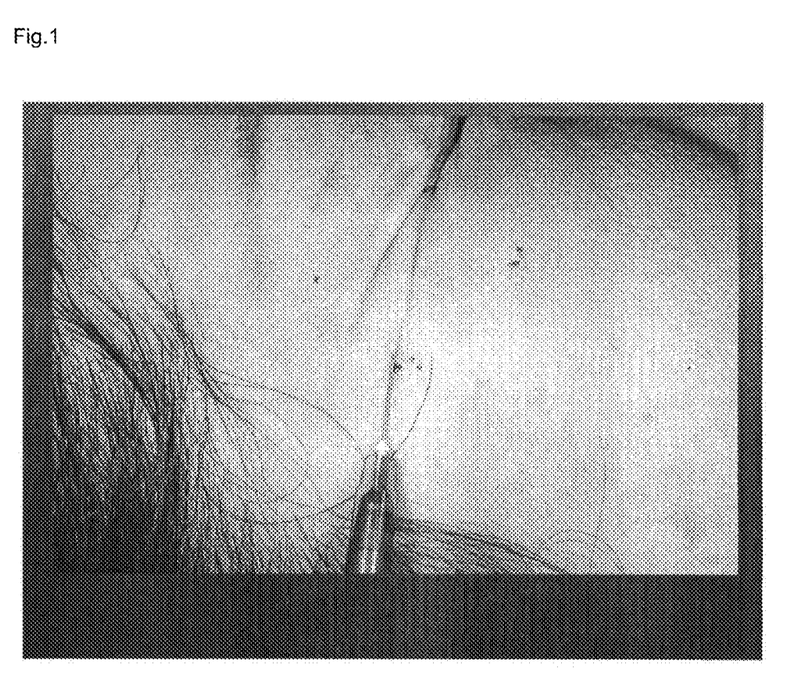
FIG. 1 It is a figure showing the injection of the formulation of the present invention into the dermis, taking the injection into the lateral angle of right eye in Case 1 as an example.
Figure 2:
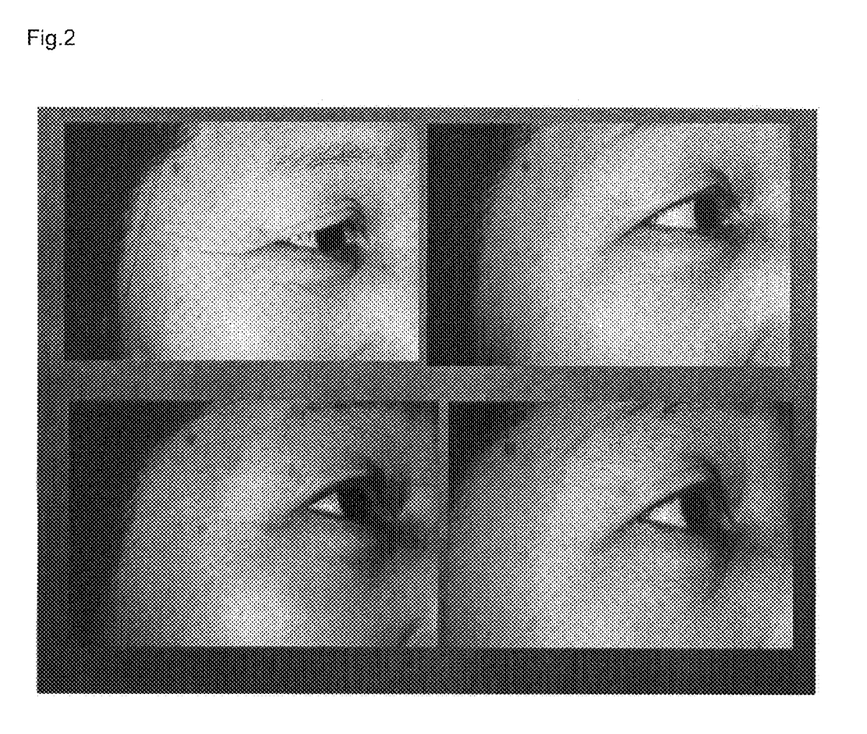
FIG. 2 It is a figure showing the conditions of the target site to be treated of Case 1 (right lateral angle of eye) before and after the injection of the formulation of the present invention (before and after the treatment).

0.8 ml of the formulation of the present invention (0.2 ml per 1 cm² of the skin of the treatment site) was injected to the dermis of the target site to be treated of a 61 years-old woman (Case 1) (lateral angle of right eye) (FIG. 1). When the treatment site was observed 1 month after the treatment, several longer wrinkles in the lateral angle of right eye and plural small wrinkles at the corner of the eyes which have been confirmed before the treatment (FIG. 2, upper left) had disappeared, and the skin texture was also clearly improved (FIG. 2, upper right). Further, after 2 months from the treatment, not only the improved condition was maintained, but improvements were observed including that skin tugor was enhanced and the eye areas were plumped up, and lateral angle of the eye was lifted up (FIG. 2, lower left). Further, 3 months after the treatment, further progress of the tendency of improvement was observed (FIG. 2, lower right).

2. Case 2

Figure 3:
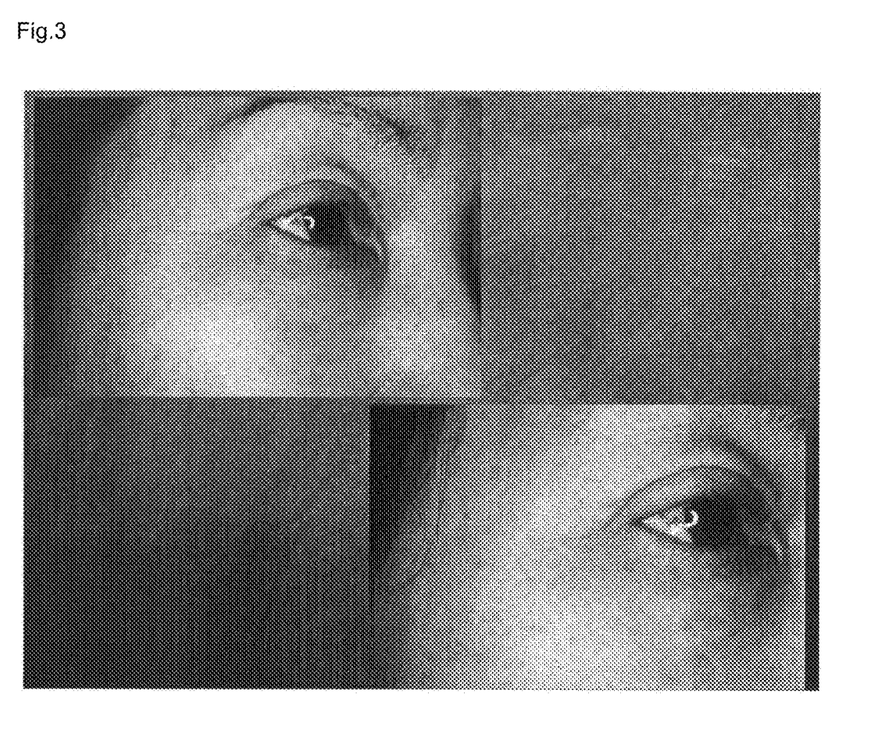
FIG. 3 It is a figure showing the conditions of the target site to be treated in Case 2 (lateral angle of right eye and inferior eyelid) before and after the injection of the formulation of the present invention (before and after the treatment).

A total of 1.6 ml of the formulation of the present invention (0.2 ml per 1 cm² of the skin of the treatment site) was injected to the dermis of the two target sites to be treated (lateral angle of right eye and inferior eyelid) of a 66 years-old woman (Case 2). When the treatment sites were observed 2 months after the treatment, plural small wrinkles at the lateral angle of right eye which have been confirmed before the treatment (FIG. 3, upper left) had diminished as the skin tugor was improved (FIG. 3, lower right). Further, 2 months after the treatment, the eye areas were plumped up and the swelling in the inferior eyelid had diminished as compared with before the treatment, and the rejuvenating effect was confirmed (FIG. 3, lower right).

3. Case 3

Figure 4:
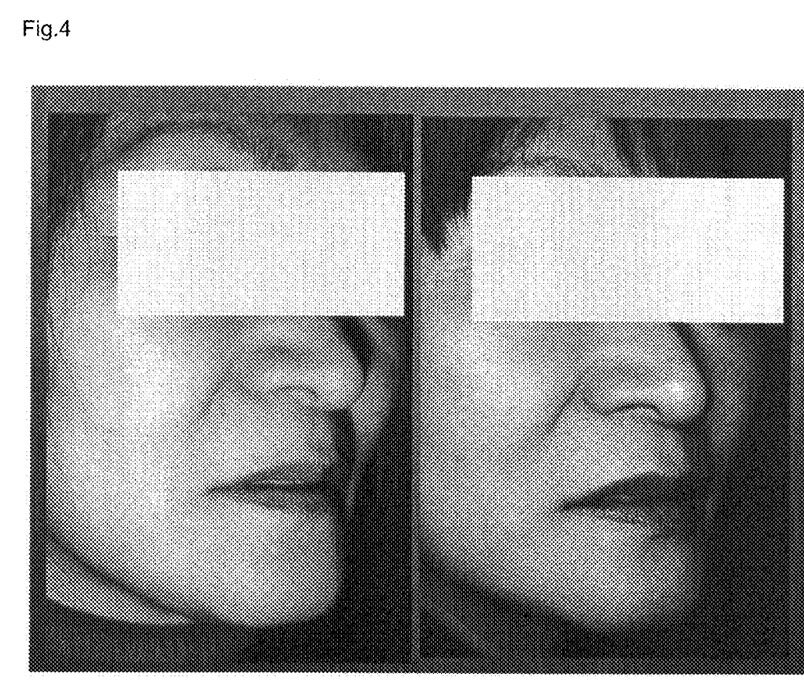
FIG. 4 It is a figure showing the conditions of the target site to be treated in Case 3 (upper lip) before and after the injection of the formulation of the present invention (before and after the treatment).

A total of 1.6 ml of the formulation of the present invention (0.2 ml per 1 cm² of the skin of the treatment site) was injected to the target site to be treated (upper lip) of a 56 years-old woman (Case 3), more specifically to the dermis of the entire width of the upper lip, which is 1 cm apart from the upper lip in the opposite direction of the bottom edge of the lip. When the treatment site was observed 2 months after the treatment, plural small wrinkles in the longitudinal direction in the upper lip which have been confirmed before the treatment (FIG. 4, left) had diminished as the upper lip was plumped up and became resilient (FIG. 4, right). Further, 2 months after the treatment, the longitudinal length of the upper lip had become shorter as the upper lip was plumped up and became steric (FIG. 4, right).

4. Case 4

Figure 5:
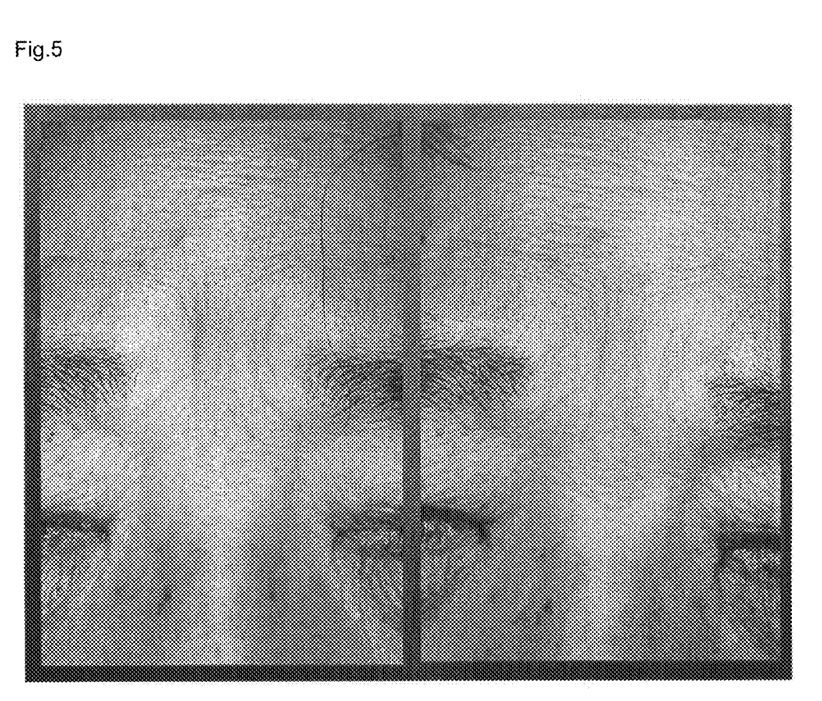
FIG. 5 It is a figure showing the conditions of the target site to be treated in Case 4 (between eyebrows) before and after the injection of the formulation of the present invention (before and after the treatment).

1.0 ml of the formulation of the present invention (0.2 ml per 1 cm² of the skin of the treatment site) was injected to the dermis of the target site to be treated (between the eyebrows) of a 68 years-old woman (Case 4). When the treatment site was observed 3 months after the treatment, plural deep wrinkles between the eyebrows which was confirmed before the treatment (FIG. 5, left) had become thinner and shorter as compared with before the treatment (FIG. 5, right). Further, the skin which was hard before the treatment was softened 3 months after the treatment, and plural small wrinkles had diminished and the skin texture was also clearly improved (FIG. 5, right).

5. Case 5

Figure 6:
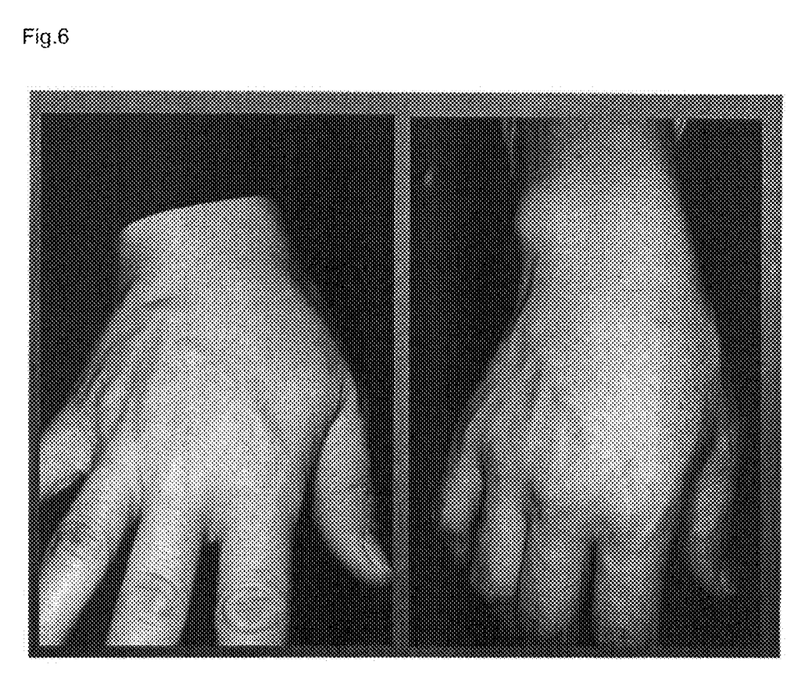
FIG. 6 It is a figure showing the condition of the target site to be treated in Case 5 (dorsum of right hand) before and after the injection of the formulation of the present invention (before and after the treatment).

3.0 ml of the formulation of the present invention (0.2 ml per 1 cm$^2$ of the skin of the treatment site) was injected to the dermis of the target site to be treated (dorsum of the right hand) of a 35 years-old woman (Case 5). The treatment site was observed 3 months after the treatment. The condition before the treatment was such that the skin was thinned and the blood vessels were clearly seen (FIG. 6, left). However, 3 months after the treatment, the skin tugor was enhanced and the swelling of the blood vessels had become less prominent, and the skin texture was also clearly improved (FIG. 6, right).

As it is stated in the above, the formulation of the present invention was shown to have a significant preventive and therapeutic effect to aging of skin.

Example 3

Test for Confirming the Effect of Preventing and Treating Scar of Skin

6. Case 6

Figure 7:
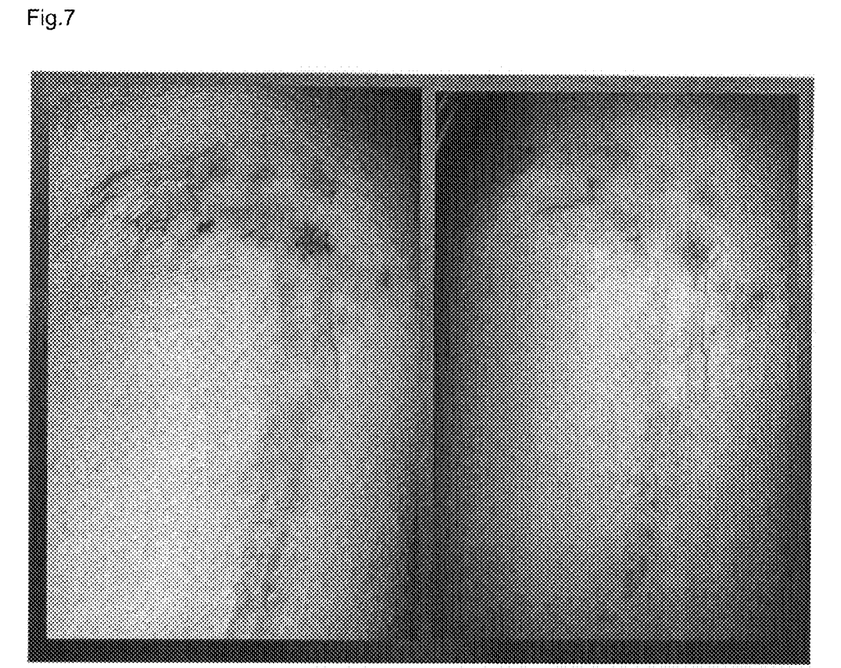
FIG. 7 It is a figure showing the conditions of the target site to be treated in Case 6 (scar on the left shoulder part) before and after the injection of the formulation of the present invention (before and after the treatment).

A 57 years-old woman with a scar (keloid) on the left shoulder part (Case 6) have had various treatments over almost 20 years for the scar, without any improvement. 1.0 ml of the formulation of the present invention (0.2 ml per 1 cm$^2$ of the skin of the treatment site) was injected to the dermis of the keloid part (marked part) on the upper part of the left shoulder in Case 6 (FIG. 7, left). When the treatment site was observed 3 months after the treatment, the keloid had become flat and the redness was faded (FIG. 7, right) as compared with the condition before the treatment (FIG. 7, left). As such, the formulation of the present invention was shown to exert a significant effect by a single operation to a refractory scar (keloid).

7. Case 7

Figure 8:
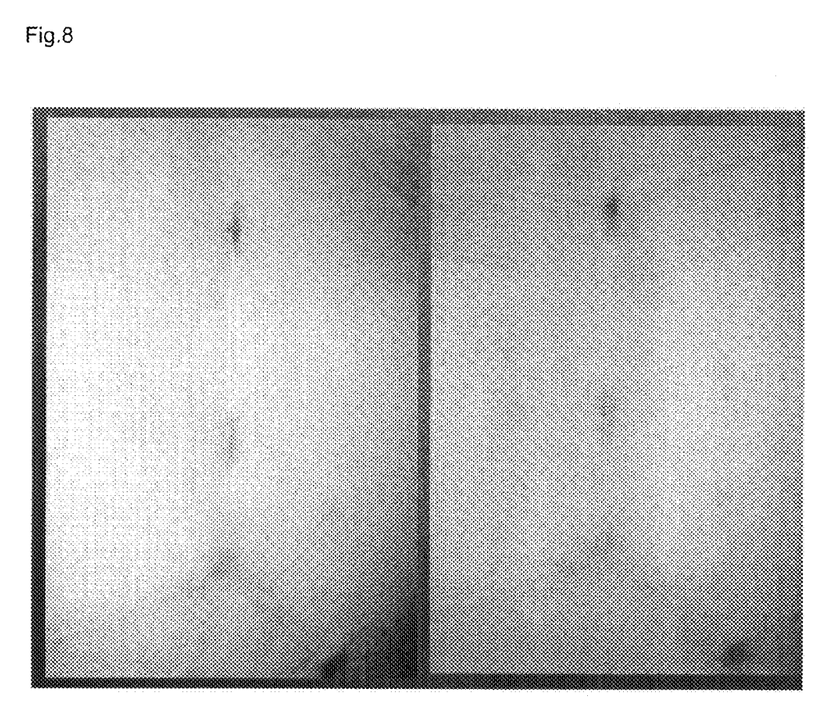
FIG. 8 It is a figure showing the conditions of the target site to be treated in Case 7 (scar on abdominal part) before and after the injection of the formulation of the present invention (before and after the treatment).

1.0 ml of the formulation of the present invention (0.2 ml per 1 cm$^2$ of the skin of the treatment site) was injected to the dermis of each target site to be treated (3 keloid parts in the abdominal part) of a 66 years-old woman with 3 scars (keloid) in the abdominal part (upper part, central part, right lower part). When the treatment sites were observed 3 months after the treatment, the keloid in the upper part had become flat and the redness of the keloid in the central part had become smaller (FIG. 8, right) as compared with the condition before the treatment (FIG. 8, left). Further, for the keloid in the lower right part, the induration under the skin and redness which were confirmed before the treatment (FIG. 8, left) had disappeared 3 months after the treatment, and the depression of skin caused by skin traction per se had almost disappeared (FIG. 8, right).

As it is stated in the above, the formulation of the present invention was shown to have a significant therapeutic effect to skin scar (keloid).

Example 4

Test for Confirming the Effect of Improving Skin Viscoelasticity

In order to confirm whether the formulation of the present invention has an effect of improving skin viscoelasticity or not, skin viscoelasticity of the dorsum of the hand in the cases was measured by using a skin viscoelasticity measurement device Cutometer MPA580 (Courage+Khazaka, Germany). Specifically, the measurement was conducted by the following method.

Figure 9:
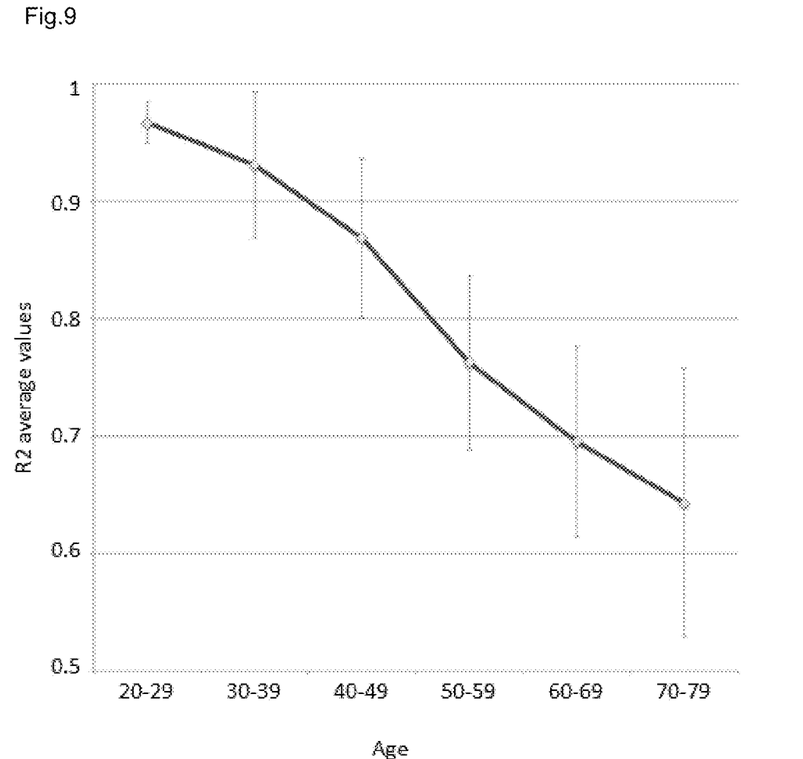
FIG. 9 It is a graph showing the R2 average values of the dorsum of the hand of normal subjects in each age group.

Prior to the measurement of skin viscoelasticity of the dorsum of the hand in the cases, the correlation formula between the skin viscoelasticity of the dorsum of the hand of a normal subject without skin diseases, and the age of the normal subject was tried to be calculated. First, a total of 60 normal subjects (10 subjects in 6 age groups (20s, 30s, 40s, 50s, 60s, and 70s to 90s)) was assembled and the skin viscoelasticity of the dorsum of the hand (20 hands for each age group; total 120 hands) was measured. The measurement was conducted in duplicate for the dorsum of one hand, and the ratio of the restoration level 2 seconds afterwards with respect to the maximum displacement value (R2=Ua/Uf) was calculated. The R2 average values for each age group are shown in FIG. 9. As it can be seen from FIG. 9, the R2 average value of the dorsum of the hand in normal subject was 96.7% in the 20s (age 20 to 29), 93.1% in the 30s, 86.8% in the 40s, 76.2% in the 50s, 69.5% in the 60s and 64.3% in the 70s to 90s. Based on these results, the correlation formula between the R2 value of the dorsum of the hand of a normal subject and his (her) age was calculated, and the following correlation formula was obtained: "age"=143.552−"R2 value"×115.347.

Figure 10:
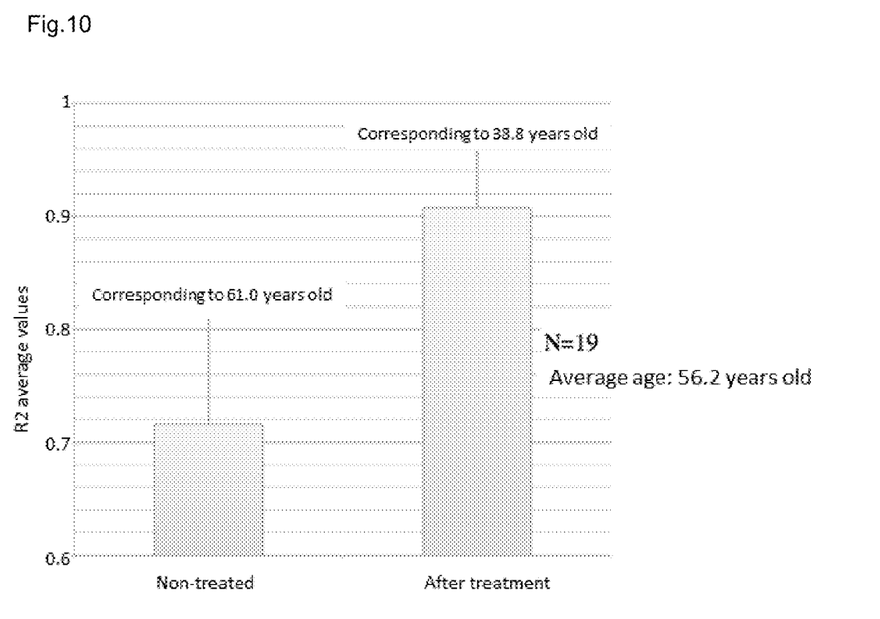
FIG. 10 It is a graph showing the R2 average values of the dorsum of the hand in the non-treated group, and the R2 average values in the treated group on the Case.

Next, 19 subjects were assembled as a case (average age 56.2), and the treatment was initiated by injecting 5.0 ml of the formulation of the present invention (0.2 ml per 1 cm$^2$ the skin of the treatment site) per day to the dermis of the dorsum of one hand, respectively. Dermis of the dorsum of the other hand was not subjected to treatment as control, and the progress was observed. Six months after the initiation of the treatment, the skin viscoelasticity (R2 value) of the dorsum of the hand where the formulation of the present invention has been injected (treated group) and that of the dorsum of the hand where no treatment was performed as control (non-treated group) were measured for all of the cases. The R2 average value of the dorsum of the hand being the treated group and the R2 average value of the dorsum of the hand being the non-treated group are shown in FIG. 10. As it can be seen from FIG. 10, the R2 average value of the dorsum of the hand being the non-treated group (not treated) was 71.6% (corresponding to 61.0 years old), while the R2 average value of the dorsum of the hand being the treated group (after the treatment) was 90.8% (corresponding to 38.8 years old). Specifically, a significant effect that the skin viscoelasticity of the dorsum of the hand was improved by a condition corresponding to 22.2 years old has been obtained with the formulation of the present invention. As such, it has been confirmed that a physiologically preferred therapeutic effect, i.e. rejuvenating effect of the skin can be obtained by the formulation of the present invention.

INDUSTRIAL APPLICABILITY

The agent for preventing and treating skin aging of the present invention exerts a significant effect on preventing and treating aging of skin such as skin wrinkle, pigmented spot, sagging skin, rough skin, skin thinning, decrease of skin viscoelasticity, etc. by an intradermal or subcutaneous administration. Further, the agent for treating skin scar of the present invention exerts a significant effect on treating an already formed skin scar by an intradermal or subcutaneous administration.

The invention claimed is:

1. A method for treating skin aging comprising administering a formulation consisting of bFGF as a sole active ingredient and one or more pharmaceutically acceptable carriers to a subject;
   wherein said formulation is administered intradermally or subcutaneously to a site of skin aging of said subject at a bFGF dosage of 1 μg/cm$^2$ to 100 μg/cm$^2$ of said site of skin aging in a single administration;
   wherein said single administration is not followed by a subsequent administration for at least two months; and
   wherein said bFGF administration results in visual reduction in wrinkles and/or increased viscoelasticity of the skin for at least two months after said administration.

2. The method according to claim 1, wherein the site of skin aging is one or more selected from the group consisting of areas of photoaging caused by disruption of dermal tissues or functional decrease of fibroblast cells, skin wrinkle, sagging skin, rough skin, skin thinning and decrease of skin viscoelasticity.

3. The method according to claim 1 wherein said subject is over 50 years old.

4. The method according to claim 1 wherein said subject is over 60 years old.

5. The method according to claim 1 wherein said site of skin aging is a site that has been exposed to ultraviolet rays.

6. The method according to claim 1 wherein the dosage amount of bFGF is 1 μg/cm$^2$ to 10 μg/cm$^2$ of said site of skin aging.

7. The method according to claim 1 wherein the site of skin aging is a wrinkle at the corner of the eye.

8. The method according to claim 1 wherein the site of skin aging is an inferior eyelid.

9. The method according to claim 1 wherein the site of skin aging is a wrinkle in the longitudinal direction in the upper lip.

10. The method according to claim 1 wherein the site of skin aging is a wrinkle between the eyebrows.

11. The method according to claim 1 wherein the site of skin aging is a wrinkle on the dorsum of the hand.

* * * * *